(12) United States Patent
Lloyd

(10) Patent No.: US 6,627,206 B2
(45) Date of Patent: Sep. 30, 2003

(54) METHOD AND APPARATUS FOR TREATING OBESITY AND FOR DELIVERING TIME-RELEASED MEDICAMENTS

(76) Inventor: Greg A. Lloyd, 12822 E. 23rd Ave., Spokane, WA (US) 99216

(*) Notice: Subject to any disclaimer, the term of this patent is extended or adjusted under 35 U.S.C. 154(b) by 0 days.

(21) Appl. No.: 09/916,038

(22) Filed: Jul. 25, 2001

(65) Prior Publication Data

US 2003/0021822 A1 Jan. 30, 2003

(51) Int. Cl.[7] .......................... A61K 9/00; A61K 9/48; A61K 9/20; A01N 25/00
(52) U.S. Cl. ................. 424/400; 424/451; 424/464; 514/909
(58) Field of Search ................. 514/909, 910, 514/911; 424/400, 464, 465, 489, 451

(56) References Cited

U.S. PATENT DOCUMENTS 5,017,381 A * 5/1991 Maruyama et al. ......... 424/472
5,417,976 A * 5/1995 Peery et al. ............... 424/438

* cited by examiner

Primary Examiner—Carlos A. Azpuru
Assistant Examiner—Micah-Paul Young
(74) Attorney, Agent, or Firm—Wells St. John P.S.

(57) ABSTRACT

An apparatus and method for treating obesity and for delivering time-released medicaments is described and which includes a plurality of space-filling portions which are sized to be received within a human patient's body and which come together in a patient's body to form a structure which provides therapeutic benefit to the patient. In the method of the present invention, the method includes providing a plurality of space-filling portions which are sized to be received within the patient's body; and inserting the space-filling portions into the body of the patient and wherein the respective space-filling portions come together following insertion into the body to form a structure providing therapeutic benefit to the patient.

21 Claims, 6 Drawing Sheets

METHOD AND APPARATUS FOR TREATING OBESITY AND FOR DELIVERING TIME-RELEASED MEDICAMENTS

BACKGROUND OF THE INVENTION

1. Field of the Invention

The present invention relates to a method and apparatus for treating obesity in humans and for delivering time-release medicaments into a patient's stomach and more particularly to a therapeutic structure which includes a plurality of space-filling portions which are sized to be received within the human patient's body and which come together in the patient's body to form a structure which provides therapeutic benefits.

2. Description of the Prior Art

The adverse health consequences of obesity are well known and established. It is clear that many interrelated behavioral and/or metabolic factors are at work. Consequently, it is extremely difficult for many obese people to lose weight on there own volition.

For obese patients at high risk of weight-related illness, and for the morbidly obese, there are a variety of available bariatric treatments. The most aggressive procedures are the various bariatric surgeries for reducing the stomach lumen. These surgeries include gastroplasty, gastric banding, intragastric balloons and gastric stapling. These methods can be highly effective because they severely limit the amount of food a person can ingest at one sitting, and depending upon the procedure, may induce a continual sense of satiety. Unfortunately, these surgical procedures are quite expensive. Further, the general poor health of this class of patient in combination with a major surgical procedure results in a high incidence of complications and mortality. In another approach utilizing minor surgery, an intragastric balloon can be positioned by way of permanently placed, percutaneous endoscopic gastrostomy tube. However, as with any permanent aperture made through the skin, special hygienic practices are required of the patient and complications often arise. Non-surgical bariatric procedures such as the placement of intragastric inflatable balloons via the esophagus, for example, require what is viewed to be an uncomfortable endoscopic procedure. Yet another non-surgical bariatric procedure entails wiring a patient's jaw shut to limit food intake. However, besides being quite embarrassing and physically uncomfortable, this procedure carries an attendant risk of aspiration of vomit so patients must carry scissors or wire cutters at all times.

Outside of the discipline of bariatrics, many patients with chronic illnesses or illnesses which must be treated over a prolonged period of time (months or weeks), must remember to administer oral medicaments on a frequent and periodic schedule. Although the consequences of the disease may be serious and even life threatening, many patients find it difficult to rigorously comply with their prescribed long-term dosing regimen. A number of alternative drug delivery technologies have been developed to address this issue. Time-released oral medicaments are one alternative which can lessen the number of pills a patient must ingest daily. However, time-released medicaments normally cannot deliver a drug beyond the duration of a single digestive cycle. Transdermal patches are another alternative. However, only a subset of drugs are compatible with this method and some patients suffer adverse reactions to the adhesives employed with same. Still further, while portable automated syringes can deliver intravenous drugs over long durations, this method however, is viewed as significantly lessening the quality of life and has inherent risks. Consequently, it is typically indicated only for treating very serious illnesses.

SUMMARY OF THE INVENTION

One aspect of the present invention is to provide a method and apparatus for treating obesity that requires little or no willpower on the part of the patient, is affordable, is relatively safe, is reversible, is physically comfortable, is substantially maintenance free, and is not viewed as being socially awkward.

Another aspect of the present invention is to provide a method and apparatus for treating obesity which is operable to displace as much as 80% of a patient's stomach lumen by the use of space-filling magnetic, biologically inert capsules which self-tessellate.

Another object of the present invention is to provide a therapeutic structure for the treatment of obesity, and for delivering time-released medicaments, which include a plurality of space-filling portions which are sized to be received within a human patient's body, and which come together in the patient's body to form a structure which provides therapeutic benefits for the patient.

A further aspect of the present invention is to provide a method for the treatment of obesity which includes the following steps: determining the volume of the patient's stomach; calculating the volume of the patient's stomach, which, if displaced, would provide medically effective weight loss; determining the number of respective space-filling portions which will form a resulting structure approximating the volume which, if displaced, would provide medically effective weight loss; providing a plurality of space-filling portions which are sized to be received within the patient's body and which come together, following ingestion, to form a structure providing therapeutic benefits for the patient.

A further aspect of the present invention is to provide a therapeutic structure for the delivery of medicaments into a patient's stomach, and wherein a plurality of space-filling portions are provided, and which are sized to be received within a human patient's body, and which come together in the patient's body to form a structure, and wherein the structure carries a medicament which is released to the patient while the structure is in the patient.

Yet a further aspect of the present invention is to provide a therapeutic structure comprising a plurality of space-filling portions which are sized to be received within a human patient's body and which magnetically come together in a patient's body to form the therapeutic structure, and wherein an application of a degaussing field in a given pattern to the therapeutic structure causes the therapeutic structure to disassociate thereby permitting the individual portions of the therapeutic structure to be passed out of the stomach and with the stool of the patient to ambient.

These and other aspects of the invention will be discussed in further detail below.

BRIEF DESCRIPTION OF THE DRAWINGS

Preferred embodiments of the invention are described below with reference to the following accompanying drawings.

FIG. 4 is an alternative form of the invention showing a greatly enlarged capsule-like structure which includes two of the space-filling portions shown in FIG. 2.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
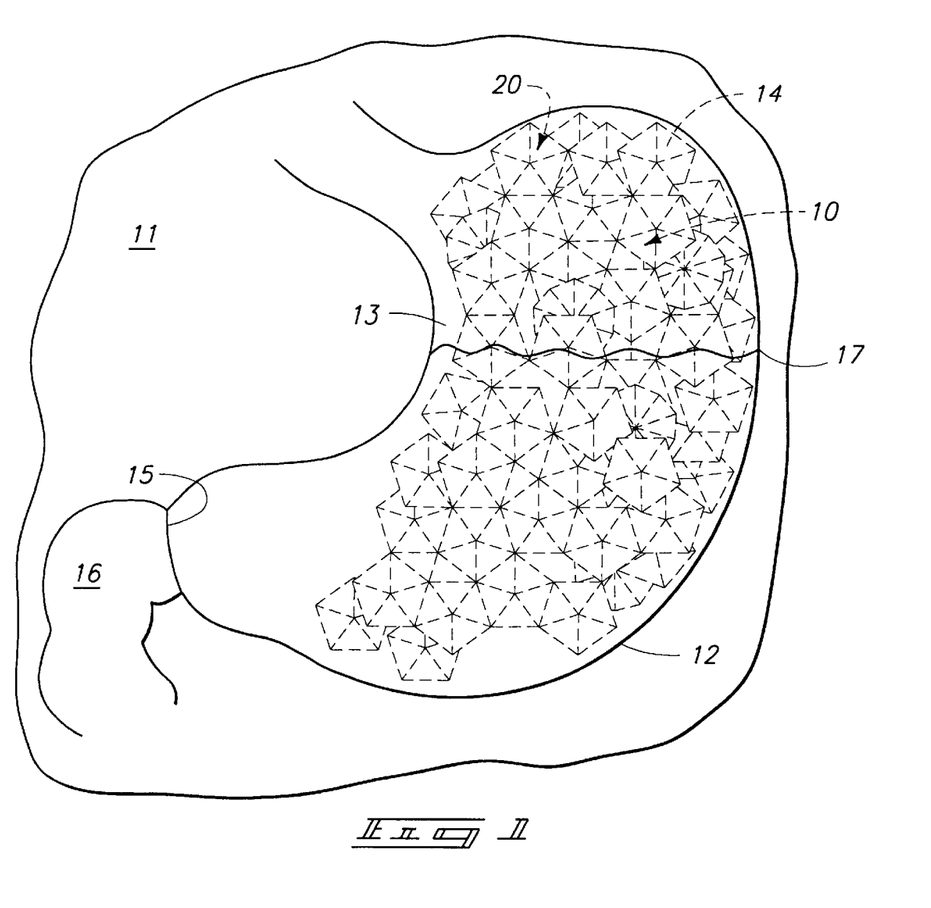
FIG. 1 is a reduced, longitudinal, vertical, sectional view taken through the stomach and part of the lower intestine of a patient and which shows the present invention.

Referring now to FIG. 1, the apparatus of the present invention is generally indicated by the numeral 10. As seen, the apparatus 10 which operates as a therapeutic structure is received within a patient's body which is partially indicated by the numeral 11. As shown, the stomach of the patient 12 is illustrated and defines a lumen 13 having a given volume. The stomach 12 includes an upper area identified as the fundus 14. Still further, the stomach lumen terminates, and the contents of the lumen 13 are emptied from the stomach 12 by way of the pylorus 15. The contents of the stomach (chyme 17) then travels into the duodenum 16 which is a portion of the patient's intestine.

Figure 2:
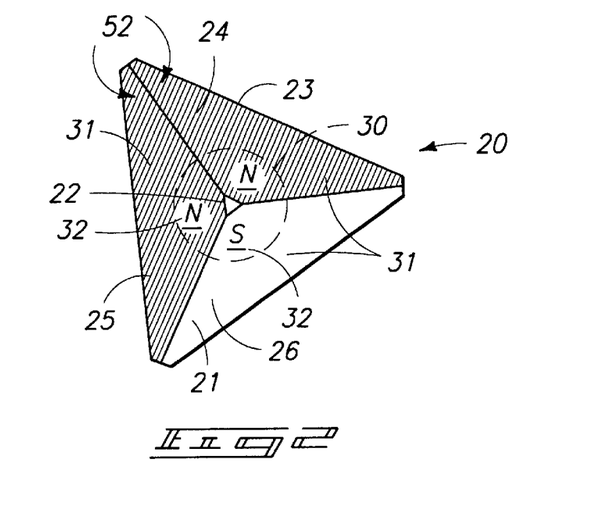
FIG. 2 is a greatly enlarged graphic depiction of a space-filling portion of the present invention showing its exterior structure and its magnetic polarities.

The apparatus 10, which forms the therapeutic structure of the present invention is comprised of individual space-filling portions which are generally indicated by the numeral 20 and which are shown more specifically in FIG. 2. As illustrated therein, it will be seen in this form of the invention that the space-filling portion 20 is formed in the shape of a true or modified tetrahedron, or a space-filling polyhedron such as a cuboid, which will be discussed in greater detail hereinafter. As seen in FIG. 2, the edges and corners may be truncated to, in part, avoid ulcerating the stomach 12. The required degree of truncation depends upon the space-filling portion's shape and the hardness of the material it is fabricated from. The main body 21 of the space-filling portion 20 includes a first end 22, representing the apex of the tetrahedron, and a second end 23 which represents the base portion thereof. As further seen in FIG. 2, a first, second, and third face 24, 25 and 26 are shown, it being understood that the fourth face, the base 27 is hidden from view but is seen more clearly in FIG. 3. As will be recognized by a study of FIG. 2, the individual space-filling portions 20 have a magnetic insert 30 shown in hidden lines. The magnetic "insert" 30 could comprise multiple curved bar magnets. In this arrangement, one for each pair of faces would be provided. In the alternative, a single, unitary assembly comprising multiple bar magnets could be employed. Whatever the form of the magnetic insert 30 it would impart magnetic polarities to the individual faces 24–27. As seen, two of the respective faces have a north polarity 31, and the two remaining faces, including the hidden base face, have a south polarity generally indicated numeral 32.

Figure 3:
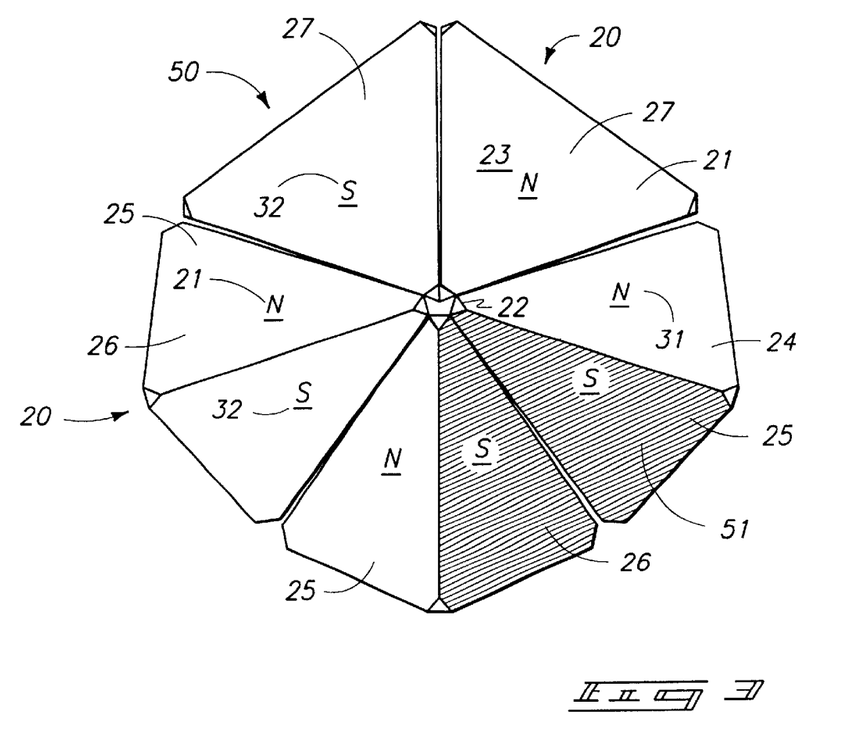
FIG. 3 is a greatly enlarged top, plan view of the apparatus of the present invention and which has formed a therapeutic structure which can provide benefit to the patient.

As seen in FIGS. 2 and 3 the required degree of truncation depends, in part, upon the shape of the respective space-filling portions 20, and the hardness of the material it is manufactured from. In view of the fact that a tetrahedron is not a true space-filling polyhedron, gaps tend to form between the respective faces 24–27 once the tessellated structure 50 is formed. In an alternative embodiment of the invention, all four faces 24–27 of the space-filling portion 20 may be rendered slightly convex in shape in order to achieve a tighter fit. As noted above, the magnetic inserts 30 provides given polarities to the faces 24–27 respectively, such that the space-filling portion 20 can, once ingested and received within the stomach 12 of the patient 11, orient itself in order to present faces with a favorable combination of polarities such that it can be magnetically attracted into any given pocket on the base structure 50. In this regard, and as seen by a study of FIGS. 2 and 3 respectively, a shaded area or pocket 51 is provided, and defined between two space-filling portions 20 that have formed into a tessellated base structure 50. This pocket 51, has two faces 25 and 26, respectively which have the polarities as shown. Referring now to FIG. 2, it will be seen that a polarity-favorable face-set 52, (which is shaded) is compatible with the pocket 51 such that it can appropriately mate or otherwise seat (tessellate) in the pocket 51. In order to promote the ability of the space-filling portions 20 to orient themselves at the greatest possible distance, the magnetic inserts 30 within the space-filling portions 20 should be fabricated of a magnetic material which exhibits a long field depth. Magnetic materials fabricated from aluminum, nickel, cobalt, copper, and iron (known in the industry as Alnico), exhibits particularly long field depths. Also, the magnetic inserts should be fabricated of a magnetic material capable of being degaussed with practical degaussing coils 80 (FIG. 7) positioned externally to the patient. To meet this end, the magnetic insert(s) 30 should be fabricated from magnetic materials which exhibit low coercive force (Hc). Cast isotropic Alnico 1 or Alnico 5 are two grades of magnetic material with particularly low Hc values of about 470 and 480 Oersted (Oe).

The content of the stomach (FIG. 1), which is often referred to as chyme 17, has acidity which ranges from about pH 2.5 to about 3.5 although on occasion it may range as low as 1.0. Accordingly, the magnetic insert(s) 30 is encapsulated within a main body 21 which is chemically stable and biologically inert. This chemically stable and biologically inert material can be selected from such materials as elastomers, thermoset or thermoplastic materials. Among the thermoplastic materials which are suitable for this purpose include fluoropolymers, and polyolefins such as low density polyethylene. Soft elastomers (from about 10 to 30 durometer) can also be a good choice for this material. In one form of the invention, the density of the space-filling portions 20 would be selected such that its specific gravity is lower than chyme 17. In this arrangement, the apparatus 10 will tend to tessellate within, and form to the shape of the fundus 14. This upper area of the stomach 12 (fundus 14) is rich in nerves responsible for signaling satiety. For example, as a patient 11 would ingest a meal, the resulting tessellated structure 10 floating atop the Chyme would permanently distend the fundus to help promote a sense of satiety or the early onset of same. Medically speaking there is no lower limit to the density of the space-filling portions 20, but practical engineering considerations would tend to limit the lower range of this density to a specific gravity of about 0.5. On the other hand, patient comfort dictates an upper limit for the density of about 2.0. As a general matter, the specific gravity would lie in a range of about 0.9 to about 1.4.

Figure 5:
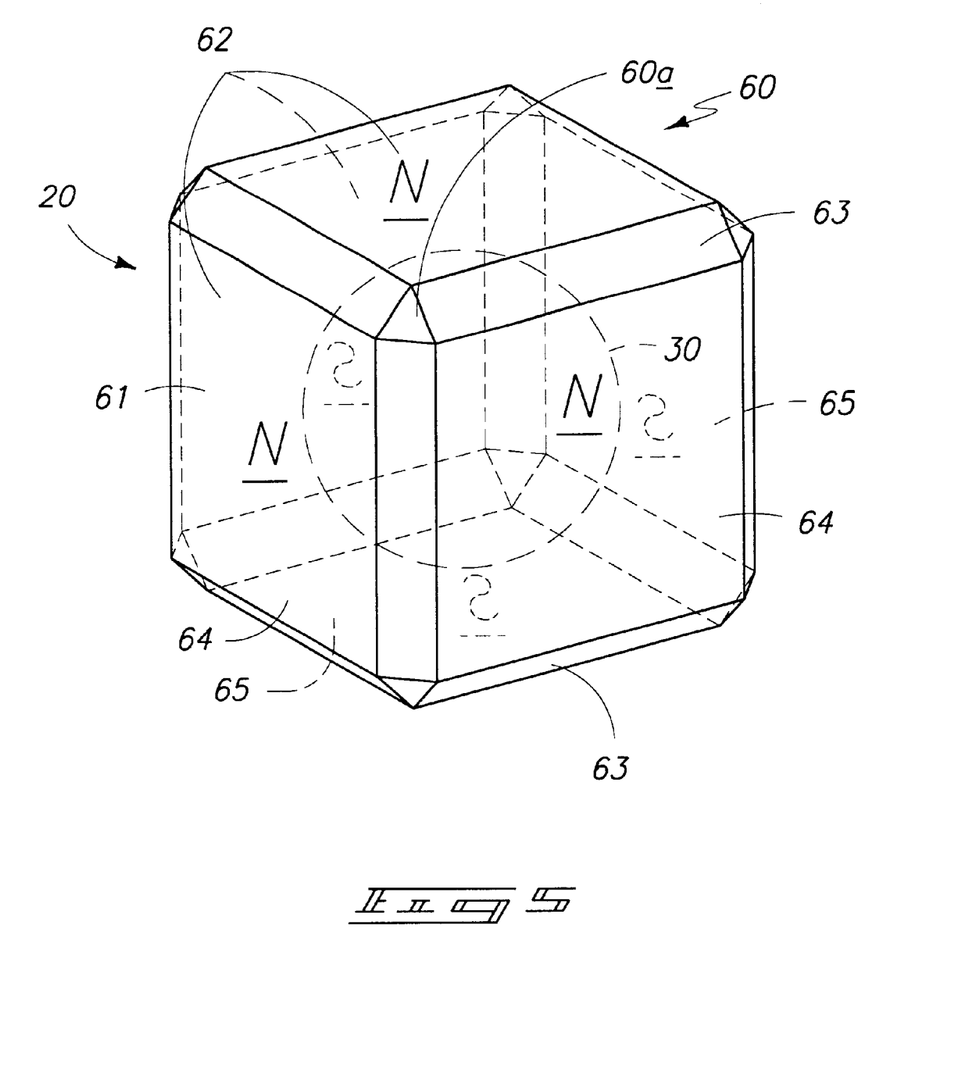
FIG. 5 is a greatly enlarged, perspective, side elevation view of an alternative form of the invention which utilizes a cube-shaped space-filling portion, and wherein the cube-shaped space-filling portion has various magnetic poles.

Referring now to FIG. 5 an alternative form of the invention 60 is shown wherein the general shape or form of the space-filling portion 20 is that of a cuboid. In the example seen in FIG. 5 a cube is shown. The cube 60 has a main body 61 which defines six substantially square faces 62. It should be noted however, that the cuboid could take the form of either the cube as seen in FIG. 5 or the square prism, that is, a polyhedron with two congruent square faces and the remaining four are rectangles. As seen in FIG. 5, the main body 61 is modified or otherwise formed to include truncated edges 63. These truncated edges avoid ulcerating the stomach and make it easier to swallow space-filling portions (20) having larger volumetric displacements. As seen in FIG. 5, each of the multiplicity of faces 62 is provided with a specific polarity by way of the magnetic insert(s) 30 which is fabricated of the magnetic material disclosed above. As seen in FIG. 5, three of the cube 60 surfaces share a common corner 60A, and have a north polarity 64; and the remaining three surfaces (in phantom lines) have a south polarity 65. This polarity configuration permits the cuboids to self-tessellate.

Figure 6:
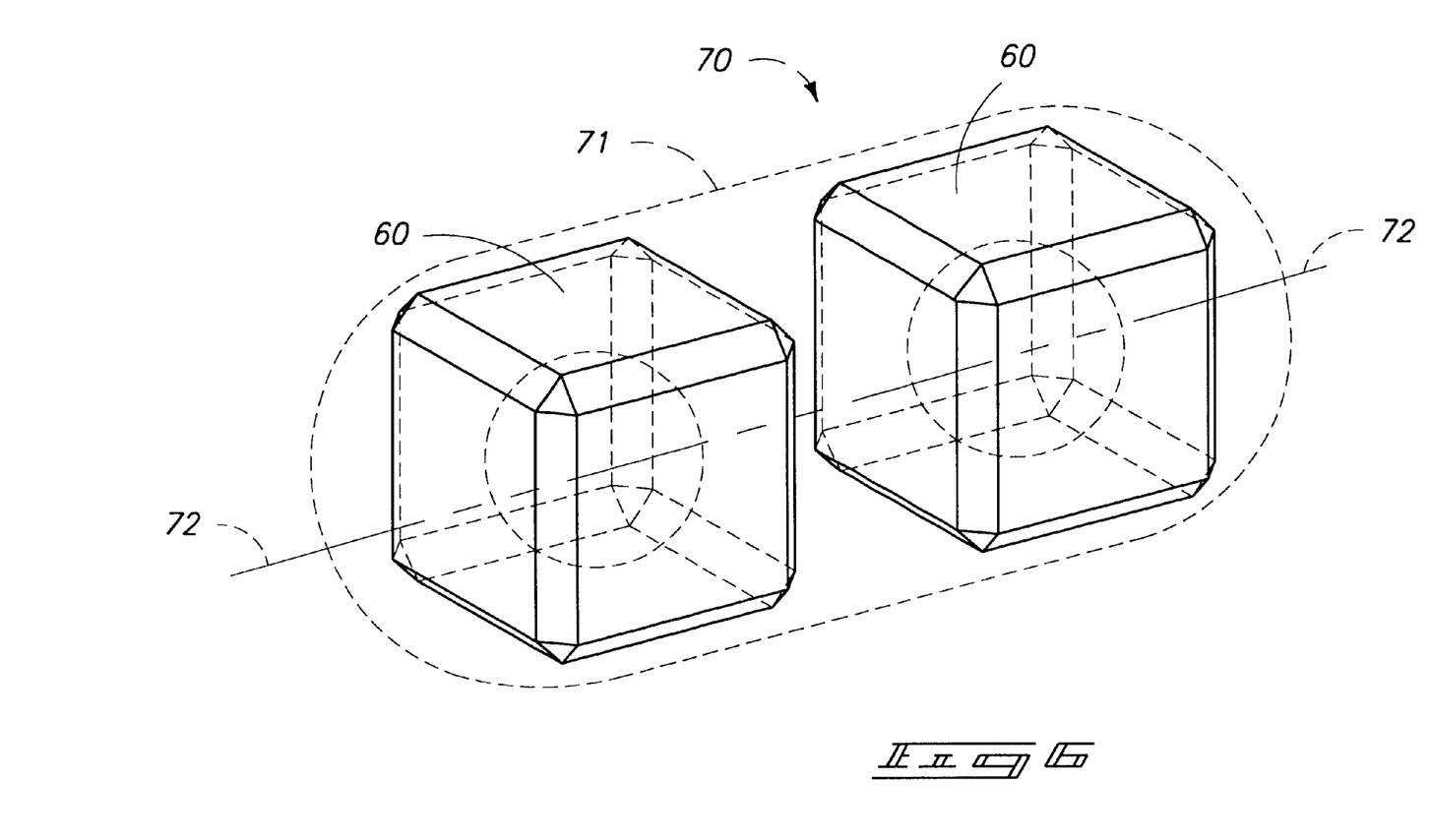
FIG. 6 is a further alternative embodiment of the present invention and which shows a pair of the space-filling portions shown in FIG. 5 in an encapsulated form.

Referring now to FIGS. 4 and 6 respectively, the space-filling portion 20, whether it be in the form of a tetrahedron, cuboid, or other space-filling shape, is enclosed within a digestible biologically degradable casing 71 which takes the form of a capsule 70. The capsule improves the swallowability for the patient 11. Suitable casing materials can be selected from one of the pharmacologically inert vitamin pill binders such as cellulose-based or gelatin/glycerin materials. A casing 71 could contain a single space-filling portion 20, or as seen in the drawings (FIGS. 4 and 6), the casing 71 may enclose two or more space-filling portions 20. In the present invention, the capsule 70 is fabricated to be the largest possible swallowable size to minimize the quantity of capsules that must be ingested. Typically, the maximum permissible dimensions for the capsule would include a cross-sectional area perpendicular to the longitudinal axis 72 of no greater than about 71 $mm^2$. This is approximately equal to a circular diameter of about 9.5 mm. Further, if fabricated with an edge, no edge of the capsule 70 would extend greater than about 5.3 mm perpendicularly from the longitudinal axis 72. Still further, the length of the capsule as measured along the longitudinal axis 72 should not be greater than about 25 to about 28.5 mm. The above mentioned dimensional limitations constrain the maximum possible volume of the respective space-filling portions 20. In this regard, if a square prism-shaped core is selected, its volume is limited to about 1.084 ml. Yet further, and as seen in FIG. 6, if twin cubes are employed, their combined volume is constrained to about 0.842 ml. Additionally, and as seen in FIG. 4, if twin tetrahedrons are employed, their combined volume is limited to about 0.222 ml. These displacement limits can be substantially increased by modestly exceeding the above limits on the capsule's maximum area and edge-dimension limits, but this would be at the expense of swallowability and patient comfort.

In order to displace 80% of an obese patient's median stomach volume of 1500 ml (just-satiated lumen volume), 1200 ml of the space-filling portions must be ingested. In the case of the structure shown in FIG. 6, a practical regimen requires that thirty capsules be swallowed, four times a day with a meal, over a period of twelve days. To successfully treat the patient using the smaller structure shown in FIG. 4, thirty capsules must be swallowed, four times a day with a meal, over a period of 45 days. Since the volume of the lumen 13 (at the onset of satiety) will typically range for any given patient from about 800 to 2200 ml, a physician must determine, in advance, the just-satiated stomach lumen of the patient 11 in order to calculate the number of capsules 70 that should be ingested.

Experience has shown that some obese individuals' nervous systems are delayed in the signaling of satiety as compared to non-obese people. Because of this observed biological phenomenon, if such an obese person is allowed to quickly binge on an especially appetizing meal, they tend to ingest about 25% more than if they eat the food at a slower pace. If the ingestion rate is not so paced, the patient will often feel gorged and may even feel the need to purge (vomit). It is not desirable to use this "gorged" stomach lumen volume as the basis for making calculations which will be utilized to determine the number of capsules 70 which must be ingested by a patient in order to experience medically effective weight loss. Accordingly, the physician should carefully consider the method to be employed in determining a particular patient's just-satiated stomach volume.

While the prior art includes a technique which utilizes radiology in combination with gas-producing granules to determine stomach volume, this technique is unnecessarily complex, and does not effectively account for patients' behavioral factors and physiology. According to the present invention therefore, a physician or clinician would determine a patient's just-satiated lumen by first pacing the ingestion rate of a liquid meal; and second, measuring the quantity of the liquid meal consumed. This can be achieved by instructing a patient to arrive on the day of testing with a relatively empty stomach. The patient would further be instructed to bring with them what they consider an especially appetizing beverage or assortment of same. These beverages should probably not have entrained gas as do ice cream products, carbonated beverages and various whipped beverages. Rather the products should include beverages such as chocolate milk; espressos; fruit juices; and fruit nectars. Measuring the liquid volume can be especially convenient if the beverages are store-bought and still in their original packaging, in which case the contents are pre-measured and labeled.

Upon arrival, the physician or clinician, based in part by interviewing the patient, and further in view of knowledge of the typical range of just-satiated stomach lumens for obese patients of the same body size and habitus, would determine the initial amount of beverage the patient would be allowed to quickly consume without concern that this initial volume is sufficient to induce satiety. This might be as much as 1000 ml for a particular patient. The beverage chosen for this initial quantity should not be of the "sports drink" variety or other rapidly digested beverage, and the physician may elect to require the patient's first drink be a relatively slowly digestible high-protein beverage. After consuming the initial quantity, the patient would next select a beverage they most desire (if there is an assortment of beverages to chose from). But they would be required, in any event, to wait for at least about 10 minutes before being allowed to ingest it. After this waiting period the patient would be allowed to slowly ingest at most about 250–300 ml of beverage at that time. This process of waiting and ingesting would be repeated until the patient achieves satiety. The total beverage volume ingested is considered to be the measure of the patient's just-satiated stomach lumen volume 13 and it is this value on which displacement calculations for the present apparatus 10 are based.

Figure 7:
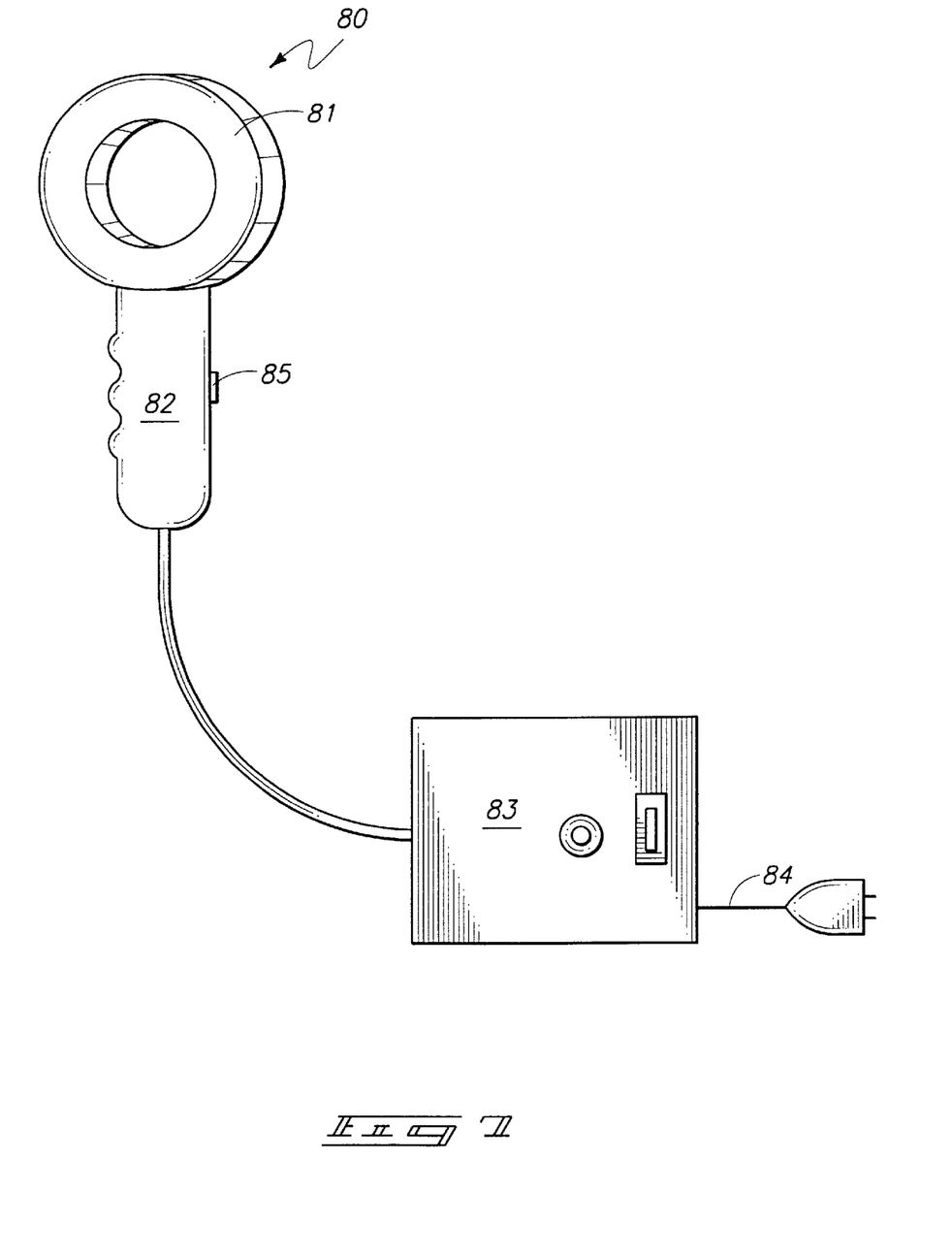
FIG. 7 is a simplistic depiction of a degaussing device employed with the present invention.
Figure 11:
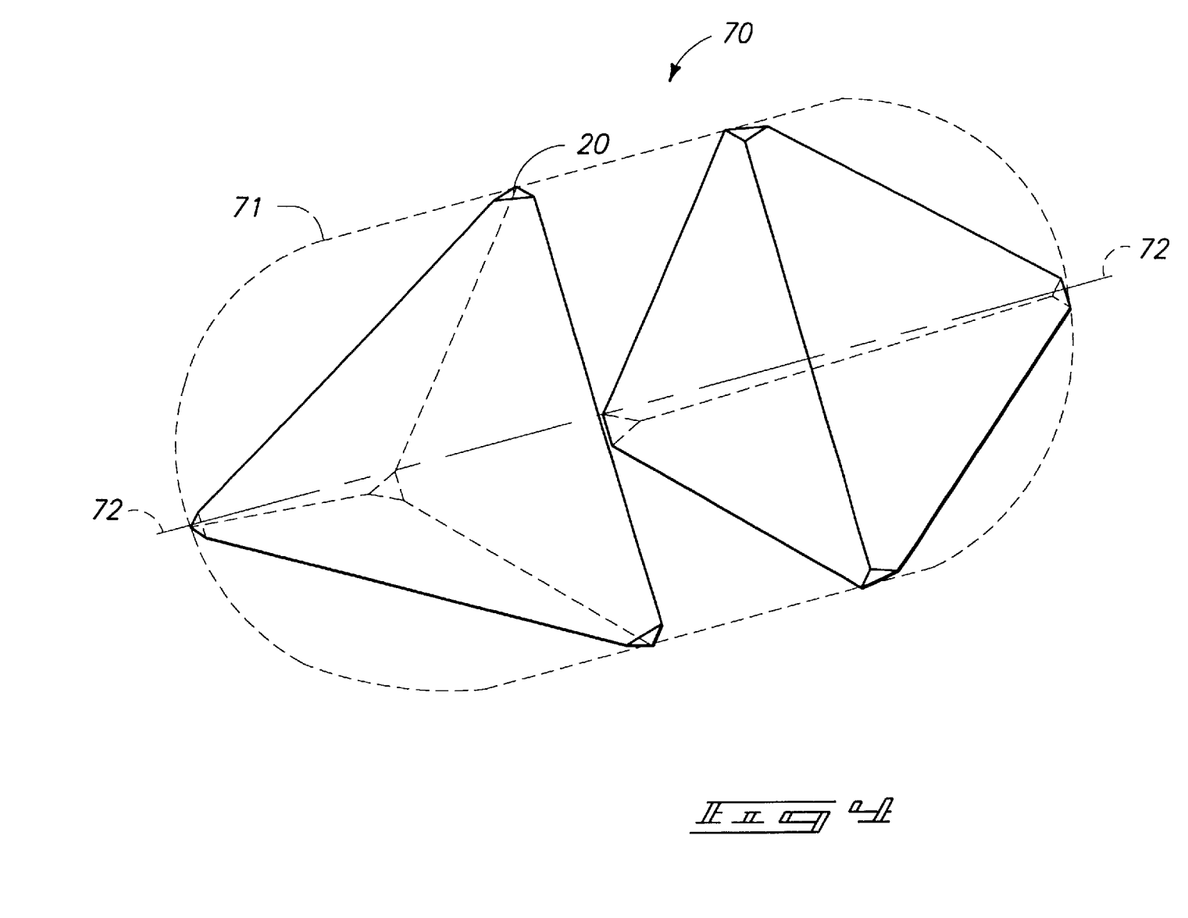

In view of the fact that any object small enough to pass through the esophagus can also pass through the pylorus, and to further prevent tessellation within the intestines and the attendant risks of bowel obstruction, the physician or clinician must ensure that the initial (first day) tessellated structure 50 which forms within the stomach 12, grows too large to pass through the pylorus 15. Accordingly, a physician or clinician should require that the patient swallow a minimum number of capsules 70 immediately after ingesting a slow-digesting liquid meal (such as a high-protein drink) at the physician's office before allowing the patient to leave. Afterwards, the capsules 70 may be self-administered on an out-patient basis. Since several space-filling portions 20 could conceivably become detached from the therapeutic structure 11, pass through the pylorus 15, and thereafter re-tessellate within the intestines to cause a bowel obstruction, patients and their physicians should maintain ready access to a degaussing instrument 80, particularly while the patient is still ingesting capsules 70. The degaussing coil 81 must generate a magnetic intensity greater than the coercivity (Hc) of the magnetic inserts 30. In the case of cast isotropic Alnico 1 (Hc=470 Oe) and Alnico 5 (Hc=480 Oe), a degaussing field intensity of 600 Oe is sufficient. Due to the extremely large size of some obese patients as well as their widely varying habitus, the degaussing coil must be able to project a working zone of the required field intensity to a distance of at least about 40 cm. Further, to permit imprecise aiming of the degaussing field, the working zone should have a diameter of at least about 6 cm. With the tessellated structure 50 degaussed, peristalsis would now force the individual space-filling portions 20 through the pylorus 15 and they would be excreted in the stool of the patient over the course of several days. The degaussing coil 81 is held by the patent by way of a handle 82. The degaussing coil 81 is coupled to a suitable power supply 83 which is coupled to a source of power by way of an electrical cord 84. The degaussing coil is selectively energized by the patient by means of a switch 85 which is mounted on the handle 82.

As noted above, one aspect of the present invention is to provide a method for the delivery of time-released medicaments to a patient suffering from chronic and/or slowly treated illnesses by utilizing the apparatus 10. This method can be implemented by utilizing biologically inert space-filling portions 20 to create a minimally sized tessellated base structure 50 which is just large enough so that it cannot pass through the pylorus 15. Thereafter, capsules 70 bearing time-released medicaments would be ingested whereupon they would self-tessellate onto the base structure 50 and thereafter release their medicament. In one possible form of the invention, the main body 21 is comprised of the extended release medicament. This particular arrangement is suitable for matrix formulations and core morphologies where there is little tendency for the matrix to spall from the magnetic insert 30. In another embodiment, the main body 21 of the space-filling portion 20 would feature a cavity (not shown) within which the medicament is located. In yet another embodiment, the capsule's casing 71 or a smaller version of same, is fabricated from the extended release medicament. As described earlier, and to ensure that the initial (first day) tessellated structure 50 is too large to pass through the pylorus 15, and to prevent the hazards associated with bowel obstructions, the physician would require that the patient swallow a minimum number of biologically inert capsules 70 as noted above, along with a slow-digesting liquid meal at the physician's office. Following this step, the base structure 50 is allowed to fully self-tessellate so that all of its magnetically active sites are freely available. This activity might require up to one full day. The patient would then be permitted to swallow the prescribed number of medicated capsules 70.

In view of the fact that drug serum concentrations produced by time-released intragastric medicaments are dependent on rates of delivery, absorption, metabolism, and excretion, a physician or other clinician may choose to initially under-prescribe the medicament and adjust it upwardly over time based on serum concentrations. This under-prescribing may be accomplished by reducing the prescribed number of medicated capsules 70 to be initially swallowed, by the strength formulation, or by a combination of both techniques.

As the medicament becomes depleted, medicament-bearing replacement capsules would be periodically ingested over a period of weeks or months to maintain the required serum concentrations. Since the base structure at the outset is minimally sized, patients would have sufficient intragastric reserve volume for many dozens to several hundred replenishments before a significant portion of the intragastric volume is displaced. Many years would typically be required to deplete this reserve volume. When the intragastric reserve volume does become depleted, a physician would degauss the patient's tessellated structure 50. Peristalsis would then force the individual magnetic inserts 30 through the pylorus and they would be expelled in the stool of the patient 11 over the course of several days. The treatment process could then of course be repeated beginning with the creation of a new base structure 50.

Operation of the Preferred Embodiments

The operation of the described embodiments of the present invention is believed to be readily apparent and is briefly summarized at this point. In its broadest aspect, the present invention relates to a therapeutic structure 10 which has a plurality of space-filling portions 20 which are sized to be received in the human patient's body 11 and which come together in a patient's body to form a structure 50 which provides therapeutic benefit to the patient. As noted above, in the discipline of bariatrics, the therapeutic structure 10 reduces the available volume of the patient's stomach 12 to induce weight loss in the patient. Still further, in the delivery of medicaments, the structure 10 is designed for the long-term release of medicaments to the patient while the structure is in the stomach 12 of the patient. As disclosed above, the therapeutic structure 10 of the present invention can, under the influence of a degaussing device 80 employed from a position outside the patient's body 11, cause the therapeutic structure 10 to disassociate and be passed out of the patient's body. Still further, where the patient's body 11 has a passageway which must be occluded, the individual space-filling portions 20 can, by application of an externally applied magnetic field, be directed to the location where occlusion is desired, and where they will then self-tessellate. Where the therapeutic structure 10 is being utilized in the treatment of obesity, the space-filling portions 20 have a volume of about 0.05 to about 2.2 ml. Still further, these structures have a specific gravity of about 1.0. Yet further, the therapeutic structure 10 of the present invention is operable to come together into a shape that is somewhat similar to the stomach lumen of the patient 11. When the therapeutic structure 10 is utilized in the treatment of obesity, the space-filling portions 20 normally have exterior surfaces which are formed from a material which is substantially biologically inert.

The method of delivering time-released medicaments of the present invention and which provides therapeutic benefit to a patient 11 includes the steps of providing a plurality of space-filling portions 20 which are sized to be received within the patient's body 11; and inserting the respective space-filling portions into the body of the patient 11, and wherein the respective space-filling portions 20 self-tessellate following insertion to form a structure which delivers a time-released medicament. In the method of bariatrics of the present invention, the patient 11 has a given stomach volume and the space-filling portions 20 form a therapeutic structure 10 in the stomach 12 which displaces the volume which provides medically effective weight loss to the patient. In connection with implementing the method of bariatrics of the present invention, before the step of ingesting the respective space-filling portions 20, the method further comprises determining the volume of the patient's stomach 12; calculating the volume of the patient's stomach, which when displaced, would provide medically effective weight loss; and determining the number of respective space-filling portions 20 which will form a resulting structure 50 approximating the volume which if displaced would provide medically effective weight loss.

These and other benefits are achieved by the apparatus and method of the present invention and which, as shown and described, avoids many of the detriments and inherent risks associated with the prior art practices and structures utilized heretofore to address the same or similar anomalies.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A therapeutic structure, comprising:
   a plurality of space-filling portions which are sized to be swalled and received in a stomach of a human patient, and which magnetically come together within the stomach of the patient to form a resulting structure which provides therapeutic benefit to the patient.

2. A therapeutic structure as claimed in claim 1, wherein the patient's stomach has a given maximum volume and the structure which forms in the patient's stomach reduces the available volume of the patient's stomach to induce weight loss in the patient.

3. A therapeutic structure as claimed in claim 1, wherein the structure carries a medicament which is released to the patient while the structure is in the stomach of the patient.

4. A therapeutic structure as claimed in claim 1, wherein the patient's body has a passageway, and wherein the space-filling portions magnetically come together to form a structure which substantially occludes the passageway of the patient.

5. A therapeutic structure as claimed in claim 1, wherein the space-filling portions have a volume of about 0.5 to about 2.2 mL.

6. A therapeutic structure as claimed in claim 1, wherein the resulting structure formed from the space-filling portions has a specific gravity of about 1.0.

7. A therapeutic structure as claimed in claim 1, wherein the resulting structure has a shape similar to the stomach lumen of the patient.

8. A therapeutic structure as claimed in claim 1, wherein the resulting structure can be influenced by an exteriorly applied magnetic field, and wherein the application of the exteriorly applied magnetic field in a predetermined pattern causes the structure to move within the patient's body.

9. A therapeutic structure as claimed in claim 1, wherein the space-filling portions have an exterior surface which is formed from a material which is substantially biologically inert.

10. A therapeutic structure, comprising:
    a plurality of space-filling portions sized to be swallowed by a patient and received in the patient's stomach, and wherein the space-filling portions magnetically comes together in the patient's stomach to form a therapeutic structure which displaces a medically effective volume of a patient's stomach lumen to cause weight loss in the patient and which further cannot be passed form the stomach.

11. A therapeutic structure as claimed in claim 10, wherein the structure displaces a volume of about 80% of the just-satiated stomach lumen.

12. A therapeutic structure as claimed in claim 11, wherein the individual space-filling portions have respective volumes of about 0.05 to about 2.2 mL.

13. A therapeutic structure as claimed claim 12, wherein the respective space-filling portions have an exterior surface which is substantially biologically inert.

14. A therapeutic structure as claimed in claim 10, wherein the respective space-filling portions have an exterior or interior surface which carries a medicament which is released to the patient while the structure is in the patient's stomach.

15. A therapeutic structure as claimed in claim 10, wherein the resulting structure has a specific gravity of about 0.1 to about 2.0.

16. A method of providing therapeutic benefit to a patient, comprising:
    providing a plurality of space-filling portions which are sized to be received within the patient's body; and
    inserting the respective space-filling portions into the body of the patient, and wherein the respective space-filling portions magnetically come together following insertion into the body to form a structure providing therapeutic benefit to the patient.

17. A method as claimed in claim 16, wherein the patient has a stomach and the space-filling portions are ingested by swallowing the individual portions, and wherein the structure formed in the stomach displaces a volume which provides medically effective weight loss to the patient.

18. A method as claimed in claim 16, wherein after the step of providing the plurality of space-filling portions, and before the step of ingesting the respective space-filling portions, the method further comprises:
    determining the volume of the patient's stomach;
    calculating the volume of the patient's stomach, which if displaced, would provide medically effective weight loss; and
    determining the number of respective space-filling portions which will form a resulting structure approximating the volume which, if displaced, would provide medically effective weight loss.

19. A method as claimed in claim 16, wherein the patient has a passageway, and wherein the space-filling portions come together to form a structure which substantially occludes the passageway of the patient.

20. A therapeutic method for providing effective weight loss in a patient, comprising:
    determining the volume of a patient's stomach;
    calculating the volume of the patient's stomach, which if displaced, would provide medically effective weight loss;

providing individually ingestible space-filling portions which are swallowed by the patient and which are received in the patient's stomach, and wherein the individual space-filling portions magnetically come together in the patient's stomach to form a resulting structure;

determining the number of respective space-filling portions which will form the resulting structure having a volume which approximates the volume which, if displaced, would provide medically effective weight loss;

ingesting the number of respective space-filling portions to form the resulting structure having the volume which will provide medically effective weight loss; and after experiencing the medically effective weight loss, and after the step of ingesting the space-filling portions, providing a source of a demagnetizing field from a location outside the patient's body and which causes the resulting structure to disassociate from one another into the individual space-filling portions, each of the individual space-filling portions passing out of the patient's stomach and body.

21. A therapeutic structure comprising:

a plurality of space-filling portions which are sized so that they may be individually ingested by a human patient, and which move together, once ingested by the human patient, to form a resulting structure which provides therapeutically effective weight loss.

* * * * *